United States Patent
Akiyama et al.

(10) Patent No.: US 11,503,855 B2
(45) Date of Patent: *Nov. 22, 2022

(54) FLAVOR INHALER

(71) Applicant: JAPAN TOBACCO INC., Tokyo (JP)

(72) Inventors: Takeshi Akiyama, Tokyo (JP); Takashi Oda, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 47 days.

This patent is subject to a terminal disclaimer.

(21) Appl. No.: 17/011,468

(22) Filed: Sep. 3, 2020

(65) Prior Publication Data
US 2020/0397045 A1 Dec. 24, 2020

Related U.S. Application Data

(63) Continuation of application No. 16/172,459, filed on Oct. 26, 2018, now Pat. No. 10,798,975, which is a (Continued)

(30) Foreign Application Priority Data

Apr. 27, 2016 (WO) .................. PCT/JP2016/063203

(51) Int. Cl.
*A24D 1/22* (2020.01)
*A24B 15/16* (2020.01)
(Continued)

(52) U.S. Cl.
CPC ............... *A24D 1/22* (2020.01); *A24B 15/16* (2013.01); *A24B 15/165* (2013.01); *A24F 40/20* (2020.01);
(Continued)

(58) Field of Classification Search
CPC ....................................................... A24D 1/22
See application file for complete search history.

(56) References Cited

U.S. PATENT DOCUMENTS 2,159,704 A 5/1939 Levey
5,027,837 A 7/1991 Clearman et al.
(Continued)

FOREIGN PATENT DOCUMENTS

CN 102144626 A 8/2011
EP 0 676 503 A2 11/1995
(Continued)

OTHER PUBLICATIONS

European Office Action for European Application No. 19 175 906.7, dated Dec. 4. 2020.
(Continued)

*Primary Examiner* — Eric Yaary
(74) *Attorney, Agent, or Firm* — Birch, Stewart, Kolasch & Birch, LLP

(57) ABSTRACT

A technique which, while avoiding excessive conduction of heat to the flavor source, reduces variance of heat conduction, and which makes it possible to reduce the weight and the cost of the flavor inhaler is disclosed. A flavor inhaler which, provided with a cylindrical holding member extending along a prescribed direction from a lighting end to a non-lighting end, includes a combustion-type heat source disposed at the lighting end, a flavor source which, in the prescribed direction, is arranged towards the non-lighting end with respect to the combustion-type heat source, and a cup-shape cup member which holds the flavor source and has a side wall and a bottom plate. The cup member is arranged with the bottom plate thereof disposed towards the non-lighting end with respect to the combustion-type heat source, and is inserted into the holding member oriented so as to open towards the lighting end or oriented so as to open towards the non-lighting end, and at least the side wall and the bottom plate configuring the cup member are configured from a material containing pulp, a binder and a metal soap.

11 Claims, 4 Drawing Sheets

Related U.S. Application Data continuation of application No. PCT/JP2017/016308, filed on Apr. 25, 2017.

(51) Int. Cl.

| | | |
|---|---|---|
| *A61M 15/00* | (2006.01) | |
| *A24F 42/00* | (2020.01) | |
| *A24F 40/30* | (2020.01) | |
| *A24F 40/20* | (2020.01) | |
| *A24F 42/10* | (2020.01) | |
| *A61M 15/06* | (2006.01) | |
| *A61M 11/04* | (2006.01) | |

(52) U.S. Cl.
CPC .............. *A24F 40/30* (2020.01); *A24F 42/00* (2020.01); *A24F 42/10* (2020.01); *A61M 15/0028* (2013.01); *A61M 11/041* (2013.01); *A61M 15/06* (2013.01)

(56) References Cited

U.S. PATENT DOCUMENTS

| | | | | |
|---|---|---|---|---|
| 5,105,831 A | * | 4/1992 | Banerjee | A24D 1/22 |
| | | | | 131/194 |
| 5,156,170 A | | 10/1992 | Clearman et al. | |
| 5,183,062 A | | 2/1993 | Ciearman et al. | |
| 5,247,947 A | | 9/1993 | Clearman et al. | |
| 5,330,622 A | | 7/1994 | Honnorat et al. | |
| 5,618,387 A | * | 4/1997 | Yeh | D21H 21/24 |
| | | | | 162/224 |
| 5,804,296 A | | 9/1998 | Itoh et al. | |
| 7,434,586 B2 | | 10/2008 | Higashi et al. | |
| 2006/0191807 A1 | * | 8/2006 | Dierken | G01G 17/02 |
| | | | | 206/242 |
| 2011/0083677 A1 | * | 4/2011 | Carroll | B65D 1/165 |
| | | | | 131/274 |
| 2012/0255696 A1 | * | 10/2012 | Ballinger | D21H 21/18 |
| | | | | 162/175 |
| 2013/0133675 A1 | | 5/2013 | Shinozaki et al. | |
| 2013/0292279 A1 | | 11/2013 | Bengtsson et al. | |
| 2015/0053219 A1 | | 2/2015 | Roudier et al. | |
| 2017/0055578 A1 | | 3/2017 | Oda et al. | |

FOREIGN PATENT DOCUMENTS

| | | |
|---|---|---|
| JP | H10-131099 A | 5/1988 |
| JP | 5-103836 A | 4/1993 |
| JP | 2013-532953 A | 8/2013 |
| JP | 2015-510399 A | 4/2015 |
| WO | WO 2012/156696 A1 | 11/2012 |
| WO | WO 2015/174442 A1 | 11/2015 |

OTHER PUBLICATIONS

Extended European Search Report dated Aug. 30, 2019 for Application No. 19175906.7.

International Search Report, issued in PCT/JP2017/016308, PCT/ISA/210, dated Jul. 18, 2017.

Notification of Transm. of Trans. of the Intl Prelim. Report on Patentability; Intl Prelim. Report on Patentability; English Trans. of Written Opinion of the Intl Searching Authority dated Nov. 8, 2018; dated Oct. 30, 2018; dated Jul. 18, 2017, issued in PCT/JP2017/016308 (Forms PCT/IB/338, PCT/IB/373 and PCT/ISA/237).

Written Opinion of the International Searching Authority, issued in PCT/JP2017/016308, PCT/ISA/237, dated Jul. 18, 2017.

Eurasian Office Action for Eurasian Application No. 201992024, dated Mar. 24, 2022, with an English translation.

First Office Action and Search Report dated Sep. 9, 2022 issued in corresponding Chinese Patent Application No. 202110324588.6, with machine translation.

\* cited by examiner

FLAVOR INHALER

CROSS REFERENCE TO RELATED APPLICATIONS

This application is a Continuation of U.S. application Ser. No. 16/172,459, filed on Oct. 26, 2018, which is a Continuation of PCT International Application No. PCT/JP2017/016308, filed on Apr. 25, 2017, which claims priority under 35 U.S.C. 119(a) to Patent Application No. PCT/JP2016/063203, filed in Japan on Apr. 27, 2016, all of which are hereby expressly incorporated by reference into the present application.

BACKGROUND OF THE INVENTION

Field of the Invention

The present invention relates to a flavor inhaler which extends in a prescribed direction from an ignition end to a non-ignition end, and particularly to a flavor inhaler having a cup member for holding a flavor source.

A flavor inhaler used to taste flavor without burning a flavor source such as tobacco has been proposed as a cigarette substitute. For example, a flavor inhaler generally includes a combustion type heat source which extends in the direction from an ignition end to a non-ignition end (hereinafter as the "lengthwise direction"), a flavor source made of a tobacco material, etc., and a holding member which holds the combustion type heat source and the flavor source.

U.S. Pat. No. 5,105,831 discloses a technique for holding a combustion type heat source and a flavor source by a container made of a heat conduction material. The container has a cup shape having a bottom plate provided with a hole through which aerosol generated by the flavor source is guided to the non-ignition end side.

WO 2015/174442 discloses a cup member made of a heat conduction material as a holding member for holding a flavor source provided in a flavor inhaler. According to the disclosure, the cup member has a claw part having at least an engagement part which engages an end face of a combustion type heat source on the non-ignition end side so that the insertion length of the combustion heat source can be adjusted.

SUMMARY OF THE INVENTION

The members for holding a combustion type heat source and a flavor source disclosed in U.S. Pat. No. 5,105,831 and WO 2015/174442 are both made of a heat conduction material such as a metal. Therefore, there is still a room for improvement on the flavor inhaler having such a conventional cup member in terms of weight reduction and cost reduction.

With the foregoing in view, it is an object of the present invention to provide a technique for reducing the weight and cost of a flavor inhaler while maintaining the performance of the conventional cup member.

According to the present invention, in order to solve the problem, a cup member for use in a flavor inhaler is made of a material including pulp, a binder, and metal soap.

More specifically, a flavor inhaler according to the present invention provided with a tubular holding member which extends from an ignition end to a non-ignition end includes: a combustion type heat source provided at the ignition end; a flavor source provided on the non-ignition end side with respect to the combustion type heat source in the prescribed direction; a cup member for holding the flavor source, the cup member being formed in a cup shape and having a side wall and a bottom plate; and a heat conduction member provided between the cup member and the holding member to cover the combustion type heat source and at least a part of a side surface of the cup member, the cup member is inserted in the holding member in such a direction that the bottom plate of the cup member is provided so as to be closer to the non-ignition end than the combustion type heat source is and the cup member is open to the ignition end side or the non-ignition end side, and the cup member is made of a material including pulp, a binder, and metal soap.

According to the present invention, using a cup member for storing a flavor source made of a material including pulp, a binder, and metal soap, the flavor inhaler can have a reduced weight or can be produced less costly.

Further features of the present invention will become apparent from the following description of exemplary embodiments (with reference to the attached drawings).

DESCRIPTION OF THE EMBODIMENTS

Here, flavor inhalers according to embodiments of the present invention will be described in conjunction with the accompanying drawings. The sizes, materials, shapes, their relative positional arrangements, etc. in the description of the embodiments are not intended to limit the technical scope of the invention unless otherwise specified.

First Embodiment

Figure 1A:
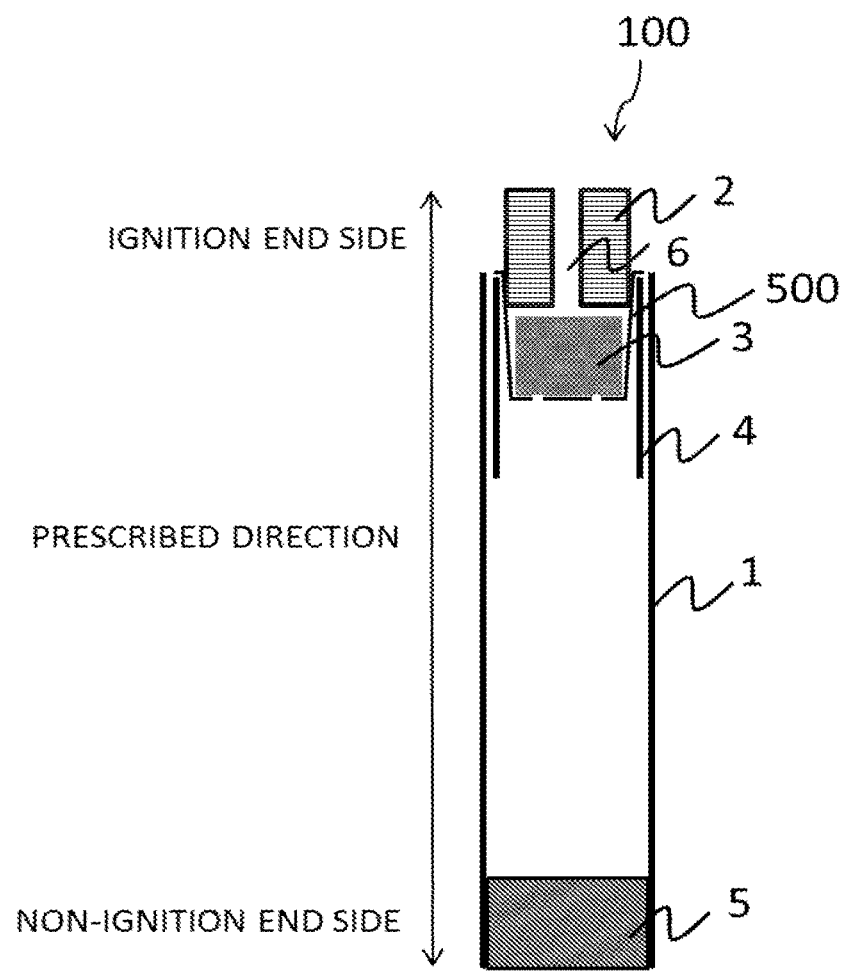
FIG. 1A is a view of a flavor inhaler according to a first embodiment of the present invention.
Figure 2:
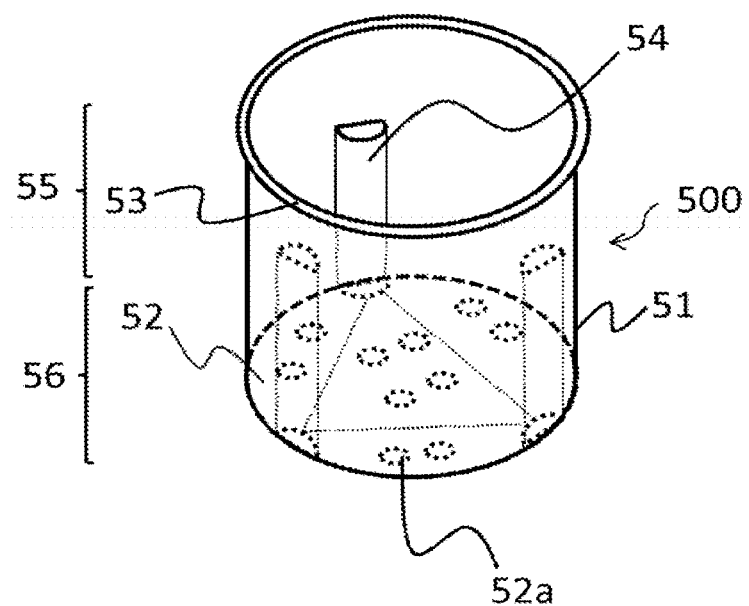
FIG. 2 is a view of a cup member according to the first embodiment.

FIG. 1A is a view of a flavor inhaler 100 according to a first embodiment of the present invention. FIG. 2 is a view of a cup member 500 according to the first embodiment.

As shown in FIG. 1A, the flavor inhaler 100 includes a holding member 1, the cup member 500, a combustion type heat source 2, a flavor source 3, a heat conduction member 4, and a filter 5. FIG. 1A shows the heat conduction member 4 but the flavor inhaler 100 may not have to include the member. According to the first embodiment, the flavor inhaler 100 does not require combustion of a flavor source.

The holding member 1 has a tubular shape which extends in a prescribed direction from an ignition end to a non-ignition end. For example, the holding member 1 has a cylindrical shape or a rectangular tube shape.

The holding member 1 may be a paper tube formed by rolling a rectangular paper sheet into a cylindrical shape and putting the edges of the paper sheet together. The kind of paper for the holding member 1 is not particularly limited but the paper is preferably paperboard. More specifically, it is preferable that the paper sheet has a basis weight from 100 g/m² to 300 g/m² and a thickness from 150 μm to 500 μm. As paper sheets for the holding member 1, two sheets of paper having a basis weight from 50 g/m² to 100 g/m² and a thickness from 90 μm to 110 μm, preferably 100 μm may be prepared and laminated on each other.

The heat conduction member 4 may cover at least a part of a side surface of the cup member 500 and may be provided between the holding member 1 and the cup member. With the presence of the heat conduction member 4, the holding member 1 and the cup member 500 can be prevented from being thermally decomposed. The heat conduction member 4 may extend further to the non-ignition end side than to an end face (a bottom plate 52 which will be described) on the non-ignition end side of the cup member 500. In this way, heat can be dissipated more efficiently from the cup member 500. Meanwhile, the end of the heat conduction member 4 on the non-ignition end side is preferably positioned so as to be closer to the ignition end than the filter 5 is.

The heat conduction member 4 may have a thickness from 10 μm to 50 μm, preferably 15 μm to 30 μm. When the heat conduction member 4 has a thickness in the preferable range, the amount of flavor generated from the flavor source 3 per puffing may be smoothed.

The heat conduction member 4 is preferably made of a metal material having a high heat conduction characteristic such as aluminum.

According to the first embodiment, the holding member 1 and the heat conduction member 4 may be layered on each other. More specifically, an aluminum-laminated paper sheet partly provided with aluminum as the heat conduction member 4 thereon may be curved into a cylindrical shape and formed on a cardboard sheet as the holding member 1. The aluminum-laminated paper sheet is preferably curved into a cylindrical shape so that the aluminum layered surface forms the inner wall. In FIG. 1A, a part of the combustion type heat source 2 and the entire side surface of the cup member 500 are covered with the heat conduction member 4, while the heat conduction member 4 is not essential, or the entire side surface of the cup member 500 does not have to be covered with the heat conduction member 4.

According to the first embodiment, when the heat conduction member 4 is provided, an adhesive (not shown) may be interposed at least partly between the cup member 500 and the heat conduction member 4. The adhesive is not particularly limited, and for example an adhesive polymer may preferably be used. As the polymer, a vinyl polymer may preferably be used, and vinyl acetate may optimally be used as a monomer for obtaining the vinyl polymer. When vinyl acetate is used as the monomer, the cup member 500 and the heat conduction member 4 may be fixed with a reduced effect on the smoking flavor.

As shown in FIG. 2, the cup member 500 has a side wall 51, a bottom plate 52, a flange 53, and ribs 54. The cup member 500 according to the first embodiment has a cup shape formed by the side wall 51 and the bottom plate 52 and holds the combustion type heat source 2 and the flavor source 3. According to the first embodiment, the cup member 500 is inserted in the holding member 1 in such a direction that the bottom plate 52 of the cup member 500 is provided on the non-ignition end side and the cup member 500 is open to the ignition end side.

According to the first embodiment, as for the size of the cup member 500, the bottom plate 52 has a diameter from 3 mm to 10 mm, preferably from 4 mm to 8 mm and a length in the direction from the ignition end to the non-ignition end (the height of the cup member 500) from 5 mm to 20 mm, preferably from 7 mm to 12 mm.

The side wall 51 has a tubular shape, and the bottom plate 52 blocks one of the pair of openings defined by the side wall 51. Note that while the end of the side wall 51 on the non-ignition side is joined to the edge of the bottom plate 52 as shown in FIG. 2, the end may extend to the non-ignition end side beyond the edge of the bottom plate 52.

The bottom plate 52 may be provided with ventilation holes 52a. The ventilation holes 52a are used to guide aerosol generated from a flavor source to the non-ignition end side. The ventilation hole 52a preferably has a diameter smaller than the particle size of a flavor source held by the cup member, preferably about in the range from 0.4 mm to 0.8 mm.

In FIG. 2 showing the first embodiment, 10 ventilation holes 52a are provided. The number and positions of the ventilation holes 52a may be adjusted, as appropriate, as will be described.

The side wall 51 may have a thickness about in the range from 0.1 mm to 0.3 mm. The thickness of the bottom plate 52 is preferably greater than that of the side wall 51 and for example may be in the range from 0.3 mm to 1.0 mm, more preferably from 0.4 mm to 1.0 mm.

The thickness difference between the bottom plate 52 and the side wall 51 may be at least 0.1 mm, preferably at least 0.2 mm. Furthermore, the thickness ratio of the bottom plate 52 to the side wall 51 may be at least 1.2, preferably at least 1.5.

The thickness range of the bottom plate 52 contributes to improvement in the heat resistance of the bottom plate 52 of the cup member which is exposed to high temperatures. This is particularly noticeable when the combustion type heat source has a longitudinal cavity 6 in the direction from the ignition end to the non-ignition end as will be described. Note that the thickness of the side wall 51 does not include the thickness of the flange 53 and the thickness of ribs 54 which will be described.

In FIG. 2, the side wall 51 is positioned substantially perpendicularly to the bottom plate 52, while the side wall 51 may be tilted to have a tapered shape so that the diameter of the opening on the ignition end side is greater than that of the bottom plate 52 as shown in FIG. 1A.

According to the first embodiment, the flange 53 has a shape which protrudes from the outer circumference of the opening of the cup member 500 to the outside of the cup member 500. As shown in FIG. 2, the flange 53 may have a shape which has a greater outer diameter than that of the tubular shape of the holding member 1 and cover the entire outer circumference of the opening of the cup member 500. A plurality of such flanges 53 may be provided intermittently along the outer circumference of the opening of the cup member 500 to protrude outwardly from the cup member 500. The flange 53 is hooked at the outer circumference of the opening of the holding member 1 as the cup member 500 is inserted in the holding member 1. In this way, the insertion length of the cup member 500 to the non-ignition end side of the holding member 1 may be adjusted.

According to the first embodiment, the end of the side wall 51 on the ignition end side and the flange 53 are joined, but the end of the side wall 51 on the ignition end side may extend in the direction toward the ignition end side beyond the end of the holding member 1 on the ignition end side. In this case, the flange 53 is hooked by the end of the holding member 1 on the ignition end side and protrudes outwardly along the outer circumference of the side wall 51.

The space in the cup member 500 according to the first embodiment includes a first space 56 (herein after also as the "first space") in the cup member 500 and a second space 55 in the cup member 500. The first space 56 may include projections like ribs 54 which project toward the center in the cup member on the inner wall side of the side wall 51. In FIG. 2, three ribs 54 are arranged at equal intervals as the projections in the first space.

According to the first embodiment, the projections arranged in the cup member 500 are in contact with the end face of the combustion type heat source 2 on the non-ignition end side, so that the combustion type heat source 2 is held in the cup member 500. As will be described, the combustion type heat source 2 and the cup member 500 may be adhered with each other by a binder.

The ribs 54 project from the inner wall surface of the side wall 51 of the cup member 500 toward the inside of the cup member 500 and forms raised parts continuously along the inner wall surface from the bottom plate 52 to the ignition end side. The length (height) of the rib 54 is preferably smaller than the height of the cup member 500 from the bottom plate 52 to the flange 53. More specifically, the position of the rib 54 at the top part on the ignition end side is preferably closer to the non-ignition end than the flange 53 is. In this way, the combustion type heat source is hooked by the top parts of the ribs 54 positioned on the ignition end side, so that the combustion type heat source is prevented from reaching the bottom plate 52 of the cup member 500, and the insertion depth can be adjusted.

The second space 55 of the cup member 500 corresponds to the space in the cup member 500 between the opening of the cup member and the top parts of the ribs 54 on the ignition end side, and the first space 56 corresponds to the space in the cup member 500 between the top parts of the ribs 54 on the ignition end side and the bottom plate 52. According to the first embodiment, the flavor source 3 may be stored in the first space 56.

According to the first embodiment, the volume of the first space is preferably greater than the volume of the second space. The length (height) in a prescribed direction of the first space is preferably greater than the second space.

In the cup member 500, a plurality of projections like the ribs 54 are preferably provided along the inner wall surface of the cup member 500, and three, four, or five such projections are more preferably provided. The plurality of ribs 54 are preferably provided at equal intervals along the inner wall surface of the cup member 500. As three to five projections are provided at equal intervals along the inner wall surface of the cup member 500, the first space 56 may have a sufficient volume, while the combustion type heat source 2 may be held in a stable manner.

Projections in a different shape may be provided instead of those having a semicircular section in the lateral direction like the ribs 54. The projecting length of the rib 54 from the inner wall surface of the first space of the cup member 500 may increase or decrease for a certain length from the bottom plate 52 to the opening. The lateral sectional shape of the rib 54 may change in the prescribed direction, or alternatively, the distance from the central axis through the center of the bottom plate 52 to each rib may be fixed. In these cases, the lateral sectional shape of the rib 54 is kept constant or changed.

The projections are not limited to those like ribs 54 which continuously extend along the inner wall surface from the bottom plate 52 to the ignition end side, and the projections need only have a sufficient size to hook the combustion type heat source. The shape of the projection is not particularly limited if the projections can be provided to form the cup member 500 as will be described.

According to the first embodiment, when the projections (ribs 54) are provided at equal intervals along the inner wall surface of the cup member 500 as shown in FIG. 2, at least some of the ventilation holes 52a are preferably provided in positions closer to the inner wall surface of the cup member 500 than the minimum distance lines (the dotted lines in FIG. 2) connecting the peaks of the semicircular sections of adjacent projections (ribs) are. Here, the peaks of the projections each has a maximum length from the inner wall surface of the cup member 500 as viewed from immediately above the opening of the cup member 500 as the upper side when the sectional shape is not semicircular or changes in the prescribed direction.

In this way, the ventilation holes are provided up to positions close to the edge of the bottom plate 52 of the cup member 500, which accelerates convection in the cup member 500, which allows the flavor source and air to efficiently come into contact and contributes to improvement in the efficiency of transferring the flavor to the non-ignition end side.

According to the first embodiment, the cup member 50 (the side wall 51, the bottom plate 52, the flange 53, and ribs 54) is made of a material including pulp, a binder, and metal soap.

Conventionally available wood pulp or the like can be used without any particular restriction.

The binder may be an organic binder, examples of which may include starch, carboxyalkyl cellulose and a salt thereof such as carboxyethyl cellulose, sodium carboxyethyl cellulose, carboxymethyl cellulose (CMC), and sodium carboxymethyl cellulose (CMC-Na), cold water-soluble polyvinyl alcohol, carboxymethylated starch, methyl cellulose, hydroxyethyl cellulose, polyacrylate, and a butenediol-vinyl alcohol copolymer.

When the binder is carboxymethyl cellulose or a salt thereof, its degree of etherification may be from 0.5 to 1.0, preferably from 0.55 to 1.0, more preferably 0.55 to 0.65. The lower limit value for the degree of etherification is 0.5, which contributes to improvement in the strength of the cup member and the fluidity thereof during forming. Meanwhile, the upper limit value for the degree of etherification is 1.0, which allows the cup member to be dried at high speed during forming.

Use of carboxymethyl cellulose or a salt thereof (such as a sodium salt: CMC-Na) allows a smoking flavor to be maintained well. According to the first embodiment, CMC-Na with an etherification degree from 0.55 to 0.65 may be used.

The number of carbons in a fatty acid forming the metal soap may be about from 12 to 20. Specifically, the fatty acid is preferably stearic acid. The non-alkali metal may be calcium, magnesium, zinc, aluminum, or strontium, preferably calcium.

Specifically, the metal soap may be one or any mixture of calcium stearate, magnesium stearate, zinc stearate, aluminum stearate, strontium stearate, calcium laurate, magnesium laurate, zinc laurate, aluminum laurate, and strontium laurate or a mixture of thereof. Among the above, calcium stearate is preferably used. The use of calcium stearate has less effect on the smoking flavor.

As described above, the cup member 500 includes the metal soap as well as the pulp and the binder.

The metal soap includes a fatty acid chain-based non-polar part and a non-alkali metal part-based polar part, is water-insoluble and water-repellent, and has a surface active function.

Therefore, it is considered that the cup member 500 according to the first embodiment including the metal soap is provided with water repellency. This is expected to suppress reduction in the aerosol delivery amount caused by adsorption of aerosol generated from the flavor source 3 stored in the cup member 500 which will be described and reduction in the rigidity of the cup member 500 caused by the aerosol adsorption.

The metal soap also has the surface active function as described above, and the mechanism of how reduction in the rigidity of the cup member 500 caused by the aerosol adsorption may be estimated as follows.

A monovalent cation salt such as metal soap is highly water-soluble. This is because its ionic strength is smaller than that of a bivalent cation salt such as a non-alkali metal.

Stated differently, the metal soap hardly dissociates in water.

Therefore, it is considered that in a water-rich environment (for example with condensation of the moisture of aerosol), the physical properties of the metal soap are unaffected and exhibited.

Meanwhile, as described above, the metal soap serves as a surfactant.

However, it is considered that OH radicals (or ionized O-radials) are densely provided on the surface of the pulp included in the cup member 500, and the cation part of the non-alkali metal is drawn or coordinate-linked to the vicinity of the pulp surface.

It is considered that when water is externally provided to the cup member 500 as a result, a long chain fatty acid part which is a hydrophobic group is in contact with the water, so that the cup member 500 including the pulp and the metal soap exhibits water repellency against the water.

The content of the pulp in the cup member may be from 30% to 70% by weight, preferably from 50% to 70% by weight. The weight ratio of the pulp and the binder in the cup member 500 may be from 25:75 to 70:30, preferably 25:75 to 45:55.

As the binder and the pulp are included in the cup member 500 in the above ranges, the strength and surface smoothness of the cup member 500 are improved.

The content of the metal soap in the cup member 500 may be 0.3% to 2.0% by weight based on 100% by weight of a mixture of the pulp and the binder.

The cup member 500 may include an appropriate flavor other than the pulp, the binder, and the metal soap.

According to the present invention, the method for producing the cup member is not particularly limited and may include injection molding. More specifically, the injection molding includes the steps of filling a molding material including water into the cavity of a mold and heating the mold thereby removing the water. Note that the mold may be heated before filling the water and the molding material into the cavity. When a cup is formed by injection molding according to the embodiment, the molding material may include pulp, a binder, and metal soap. More specifically, when the material includes a mixture of 30% to 70% by weight, preferably 50% to 70% by weight of pulp and 20% to 60% by weight, preferably 20% to 40% by weight of a binder (where the weight ratio of the pulp and the binder is from 25:75 to 70:30, preferably from 25:75 to 45:55), and 0.3% to 2.0% by weight of metal soap based on 100% by weight of the mixture of the pulp and the binder, 30% to 100% by weight of water based on 100% by weight of the total weight of the pulp and the binder is added to the material, and thus the material after adding water may be obtained. When the cup member is produced by integral molding, the method may include the step of kneading the material, thereby preparing a molding material and filling the molding material in the cavity of a mold having a mold surface for forming the cavity heated to a temperature from 120° C. to 240° C., preferably from 160° C. to 220° C. The water contained in the material may be removed by filling the material in the cavity of the high temperature mold. According to the embodiment, the molding material includes metal soap. The metal soap contributes to improvement in the water repellency of the cup member as described above and also to improvement in the moldability during molding. More specifically, the presence of the metal soap in the molding material allows better release from the mold to be achieved. In this way, defects in the shape of an obtained cup member can be reduced, or the difference between the shape of the mold and the shape of an actually obtained cup can be reduced.

According to the first embodiment, the cup member 500 is made of a material including plp, a binder, and metal soap, and therefore the cup member can have a smaller weight than a conventional metal cup member, and the material cost can be reduced. Using the above-described material as the material of the cup member, the cup member 500 having a reduced thickness and higher rigidity can be produced.

When the cup member 500 is produced by integral molding, the number of steps necessary for producing the flavor inhaler can be reduced, which contributes to reduction in the cost.

Instead of integral molding, the cup member may be obtained by adhering parts obtained by molding the material for the cup member in advance with any of the listed binders (such as carboxymethyl cellulose).

The case will be described specifically with reference to cup member 500.

(1) A part corresponding to the bottom plate 52 of the cup member 500 and a part corresponding to the side wall 51 having the flange 53 may be molded separately, and these parts may be assembled and adhered with each other.

(2) A part having the bottom plate 52 and a part of the side wall 51 of the cup member 500 and a part having the remaining part of the side wall 51 and the flange 53 may be molded separately, and these parts may be assembled and adhered with each other. For example, two parts divided in the up-down direction as viewed from the side of the side wall 51 may be molded, and these parts may be adhered with each other.

(3) The parts of the cup member 500 except for the flange 53 and a part corresponding to the flange 53 may be molded separately, and these parts may be assembled and adhered with one another.

(4) Two parts corresponding to the left and right parts of the cup member 500 as viewed from the opening side (from immediately above) may be molded separately, and these parts may be assembled and adhered with one another.

(5) The parts of the cup member 500 except for the ribs 54 and parts corresponding to the ribs 54 may be molded separately, and these parts may be assembled and adhered with each other.

(6) The shapes of the separately molded parts in (1) to (5) may be changed as appropriate, or the number of the parts may be increased from two to three or more. The above-described parts may be formed by injection molding as described above.

As shown in FIG. 1A, the combustion type heat source 2 has a pillar shape which extends from the ignition end to the non-ignition end. The combustion type heat source 2 has a longitudinal cavity 6. The longitudinal cavity 6 extends from the ignition end to the non-ignition end through the combustion type heat source 2. The longitudinal cavity 6 is provided through the combustion type heat source 2, so that a flavor source is heated by convection heat transfer.

The longitudinal cavity 6 is preferably provided substantially in the center of the combustion type heat source 2 in a lateral section.

The combustion type heat source 2 may be provided with a groove (not shown) in communication with the longitudinal cavity 6 at an end face on the ignition end side. The groove may be exposed to the side surface of the combustion type heat source 2. As for the groove, two such grooves may preferably be formed perpendicularly to each other at the end face on the ignition end side. The groove may have a width in the range from 0.5 mm to 0.8 mm and a depth about in the range from 2.0 mm to 4.0 mm.

The combustion type heat source 2 may have a cylindrical shape or a polygonal cylinder shape.

The combustion type heat source 2 is made of a combustible material. The combustible material may be a mixture including a carbon material, an incombustible additive, a binder (either organic or inorganic), and water. The carbon material may preferably be removed of a volatile impurity by heating treatment or the like.

According to the first embodiment, the combustion type heat source 2 is partly fitted into the second space 55 of the cup member 500. At the time, a binder (such as sodium carboxymethyl cellulose) may be applied at a part of the inner surface of the side wall 51 of the second space 55, for example at least at one point in the vicinity of the opening, preferably at two points, and the combustion type heat source 2 and the cup member 500 may be adhered with each other. When the combustion type heat source 2 and the cup member 500 are adhered with each other, the combustion type heat source 2 can be prevented from coming off from the cup member 500. In the cup member made of a metal material, there is less affinity between the binder and the metal, and therefore the cup member and the combustion type heat source cannot be adhered with each other easily.

The combustion type heat source 2 preferably includes 30% to 70% by weight, preferably 30% to 45% by weight of a carbon material based on 100% by weight of the weight of combustion type heat source 2. When the content of the carbon material in the combustion type heat source 2 is as described above, combustion characteristics such as supply of the heat quantity and ash compacting can be improved.

The organic binder which can be used for the combustion type heat source may be a mixture including at least one of CMC-Na (sodium carboxymethyl cellulose), CMC (carboxymethyl cellulose), alginate, EVA, PVA, PVAC, and saccharides.

The inorganic binder which can be used for the combustion type heat source may be a mineral-based binder such as refined bentonite or a silica based binder such as colloidal silica, water glass, and calcium silicate.

The combustion type heat source includes preferably 1% to 10% of CMC-Na, more preferably 1% to 8% by weight of CMC-Na based on 100% by weight of the weight of combustion type heat source 2.

The incombustible additive may be a carbonate or oxide including sodium, potassium, calcium, magnesium, and silicon. The combustion type heat source 2 may include 40% to 89% by weight of the incombustible additive based on 100% by weight of the weight of the combustion type heat source 2. Furthermore, when calcium carbonate is used as the incombustible additive, the combustion type heat source 2 may include 45% to 60% by weight of the incombustible additive.

The combustion type heat source 2 does not have to have a homogeneous material over the entire locations and may include a material with a different composition in some locations of the combustion type heat source.

According to the first embodiment, the length of the combustion type heat source 2 from the ignition end to the non-ignition end (the length in the prescribed direction) may be from 5 mm to 30 mm, preferably 10 mm to 20 mm. The lateral size of the combustion type heat source 2 (the length in the direction orthogonal to the prescribed direction) may be from 3 mm to 15 mm. The lateral length of the combustion type heat source 2 having a cylindrical shape corresponds to the outer diameter of the cylinder. When the combustion type heat source does not have a cylindrical shape, a maximum value for the length in the lateral direction is the lateral size.

According to the first embodiment, the length of the combustion type heat source 2 exposed from the holding member 1 (projection length) may be from 5 mm to 15 mm, preferably from 5 mm to 10 mm. Meanwhile, the length of the combustion type heat source 2 inserted in the holding member 1 may be from 2 mm to 10, preferably from 1 mm to 4 mm.

According to the first embodiment, the flavor source 3 is adjacent to the non-ignition end side with respect to the combustion type heat source 2 in the prescribed direction. The flavor source 3 may include a plurality of flavor pieces or a single flavor source. For example, a tobacco material may be used as the flavor source 3. When for example a plurality of flavor sources are made from tobacco materials, the tobacco materials may be shredded tobacco generally available for cigarettes or granular tobacco for nasal snuffing.

The single flavor source may be used as a tobacco sheet such as a reconstituted tobacco sheet.

The flavor source 3 may also include an aerosol source such as glycerin and propylene glycol and a desired aromatic in addition to the tobacco material. When a tobacco material is used as the flavor source 3, the grain size may be from a sieve particle size of 1.4 mm pass to 0.71 mm on. In an alternative case in which a tobacco material is used as the flavor source 3, the grain size may be a sieve particle size from 1.7 mm pass to 1.18 mm on.

The flavor source 3 may contain water, the content of which may be 30% by weight or less, preferably 15% by weight or less, more preferably 10% by weight or less based on the total amount of the flavor source 3.

The water content can prevent the cup member 50 from softening or deforming when the flavor inhaler is used.

According to the first embodiment, the flavor source 3 is held in the first space 56 in the cup member 500.

According to the first embodiment, the filter 5 is provided inside the end of the holding member 1 on the non-ignition end side. According to the first embodiment, while the filter 5 is provided in the holding member 1 so that a gap is present between the cup member 500 and the filter, the invention is not limited to this arrangement. For example, the filter 5 may be provided in abutment against the cup member 500.

The filter 5 may include a filter member of cellulose acetate, paper, or any of other appropriate known filter materials. The filter 5 may include a volatile flavor component or a capsule having an aromatic as a content.

In FIG. 1A illustrating the first embodiment, the outer circumference of the filter 5 is covered with the holding member 1.

Figure 1B:
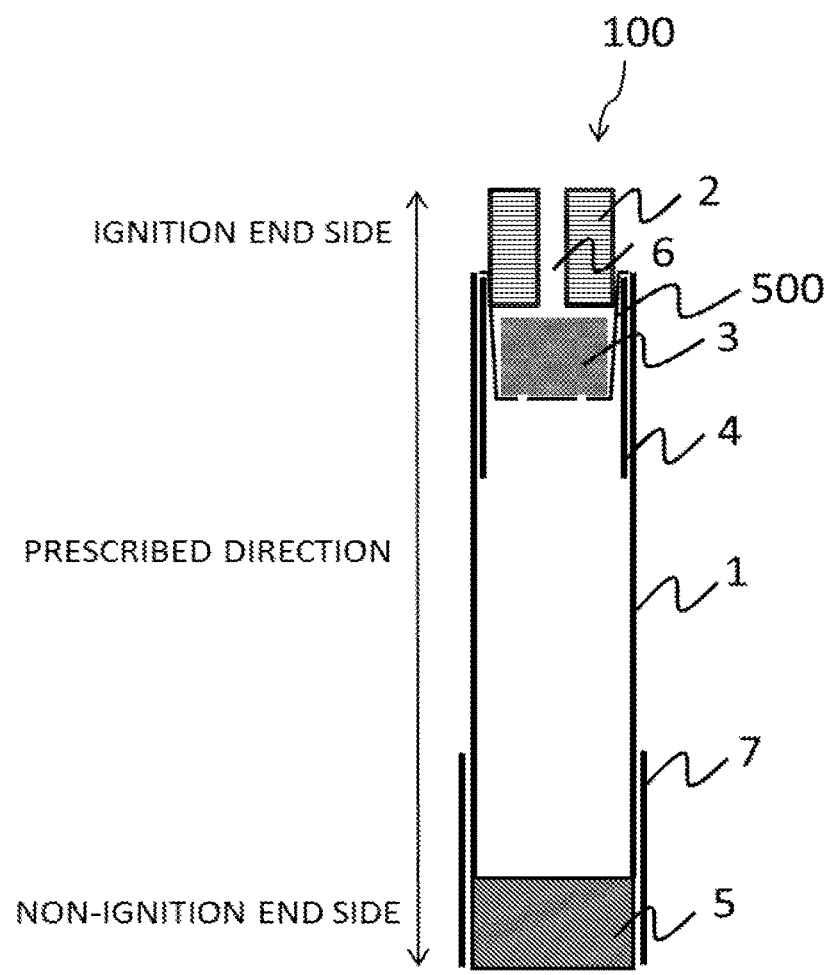
FIG. 1B is a view of an exemplary inhaler according to the first embodiment in which the positional relation between a holding member 1 and a filter 5 is different from that in FIG. 1A.

FIG. 1B illustrates an example in which the positional relation between the holding member 1 and the filter 5 are changed from the above. As shown in FIG. 1B, the filter 5 may be provided in contact with an end of the holding member 1 on the non-ignition end side. More specifically, the end of the holding member 1 on the non-ignition end side and the end of the filter 5 on the ignition end side are opposed, and the holding member 1 and the filter 5 may be connected by a connection member which covers the outer circumferences of the holding member 1 and the filter 5. The connection member is not particularly limited, and a member of paper, a film, or a thin metal film may be used, while paper is preferably used. A tipping paper sheet for connecting a rolling paper sheet and a filter in a cigarette may preferably be used as such paper for the connection member.

In this example, the end of the heat conduction member 4 on the non-ignition end side is positioned so as to be closer to the ignition end than the end of the connection member 7 on the ignition end side is. Note that the heat conduction member 4 is not essential as described above.

Second Embodiment

Figure 3:
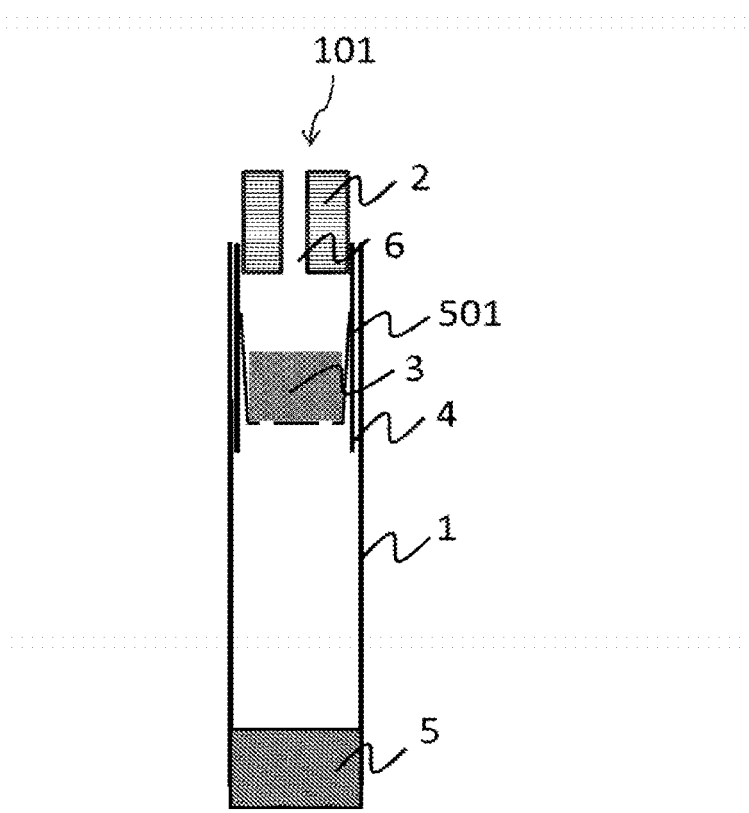
FIG. 3 is a view of a flavor inhaler according to a second embodiment of the invention.

FIG. 3 is a view of a flavor inhaler according to a second embodiment of the invention. The elements are the same as those of the first embodiment, and the flavor inhaler 101 includes a holding member 1, a cup member 501, a combustion type heat source 2, a flavor source 3, a heat conduction member 4, and a filter 5. Note that similarly to the first embodiment, the heat conduction member 4 is not essential according to the second embodiment.

The following description concentrates on the cup member 501 which is different from the first embodiment. According to the second embodiment, the cup member 501 does not have a flange protruding outwardly from the cup member 501 from the outer circumference of the opening. The side wall of the cup member 501 is tilted to form a tapered shape so that the diameter of the opening of the cup member 501 on the ignition end side is greater than the diameter of the bottom plate.

The same conditions as the first embodiment may be applied as for the size of the cup member 501, the thicknesses of the side wall and the bottom plate, and their ratios.

The same conditions as the first embodiment may be applied as for the projections which may be provided on the inner wall surface of the cup member 501 or ventilation holes which may be provided at the bottom plate 52 of the cup member 501.

The combustion type heat source 2 and the cup member 501 are not in abutment, and there is a gap between the combustion type heat source 2 and the cup member 501. Heat from the combustion type heat source 2 is transmitted to the cup member 501 and the flavor source 3 held therein through the heat conduction member 4. The combustion type heat source 2 and the heat conduction member 4 are in abutment, so that when the heat position of the combustion type heat source reaches the vicinity of the heat-conductive material, the combustion heat source can more surely be extinguished. The presence of the gap between the combustion type heat source 2 and the cup member 501 may suppress excessive heat storage in the cup member 501.

Similarly to the cup member 500 according to the first embodiment, the cup member 501 according to the second embodiment having at least the side wall 51 and the bottom plate 52 is made of a material including pulp, a binder, and metal soap. The same conditions as those according to the first embodiment may be applied as for the manufacturing method therefor, the elements of the cup member, and the composition of the materials. Similarly to the first embodiment, the cup member 501 may be an integrally molded product or obtained by adhering a plurality of parts previously obtained by molding.

Similarly to the first embodiment, an adhesive may be provided between the heat conduction member 4 and the cup member 501. The same adhesive as the adhesive according to the first embodiment may preferably be used, so that the cup member 501 and the heat conduction member 4 can be fixed with a reduced effect on the smoking flavor.

According to the second embodiment, the same conditions as those according to the first embodiment may be applied as for the materials and positional relations of the holding member 1, the combustion type heat source 2, the flavor source 3, the heat conduction member 4, and the filter 5.

According to the second embodiment, the same advantageous effects obtained for the cup member 500 according to the first embodiment may be provided.

A part of the features of the first embodiment and a part of the features of the second embodiment may be combined as appropriate to produce a flavor inhaler.

Third Embodiment

Figure 4:
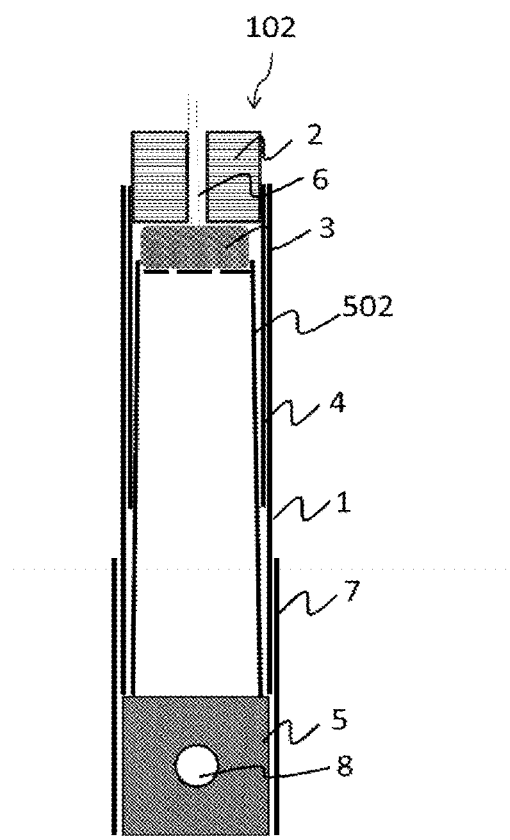
FIG. 4 is a view of a flavor inhaler according to a third embodiment of the invention.

FIG. 4 is a view of a flavor inhaler according to a third embodiment of the present invention.

The basic elements are substantially identical to those of the first and second embodiments, and the flavor inhaler 102 includes a holding member 1, a cup member 502, a combustion type heat source 2, a flavor source 3, a heat conduction member 4, and a filter 5. Note that similarly to the first and second embodiments, the heat conduction member 4 is not essential according to the third embodiment.

According to the first and second embodiments, the cup member 500 or 501 is inserted in the holding member 1 so that the opening of the cup member is positioned on the ignition end side, while according to the third embodiment, the cup member 502 is inserted in the holding member 1 so that the opening of the cup member is positioned on non-ignition end side. Note that according to the third embodiment, the combustion type heat source 2, the flavor source 3, and the cup member 502 may previously be aligned and then rolled up by the holding member 1 (may be produced by rolling).

Figure 5:
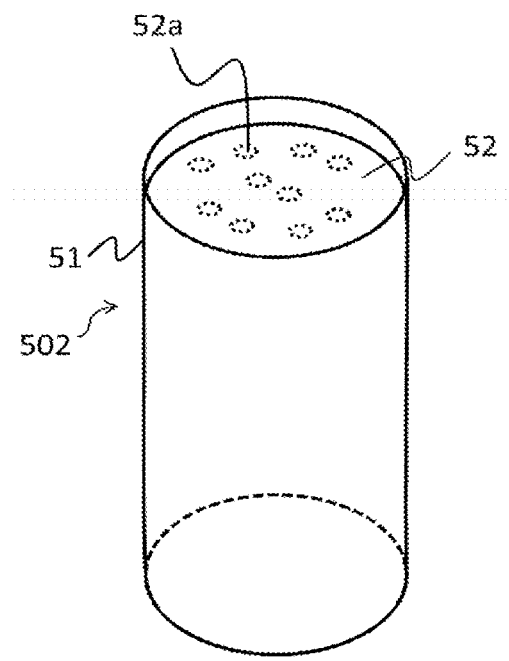
FIG. 5 is a view of a cup member according to the third embodiment.

FIG. 5 is a view of the cup member 502 according to the third embodiment. The cup member 502 has the side wall 51 and the bottom plate 52. According to the third embodiment, the flavor source 3 is held between the combustion type heat source 2 and the bottom plate 52 of the cup member 502. Alternatively, according to the third embodiment, the flange 53 may extend to protrude to the outside of the cup member 502 from the opening of the cup member 502. In this case, the flange 53 may be in abutment against the end of the holding member 1 on the non-ignition end side (not shown).

As shown in FIG. 5, the end of the side wall 51 of the cup member 502 on the ignition end side may extend closer to the ignition end than the bottom plate 52 does. In this manner, the extended side wall 51 form a circumferential wall which surrounds the end face of the cup member 502 on the ignition end side.

Alternatively, the end of the side wall of the cup member 502 on the ignition end side may extend to the edge of the bottom plate 52 to be connected to the edge of the bottom plate 52.

According to the third embodiment, the bottom plate 52 of the cup member 502 is provided with ventilation holes 52a. The ventilation holes 52a are preferably arranged in a distributed manner and as close as possible to the side wall 51. In this manner, air convention is accelerated in the space of the cup member 502, which allows the flavor source and air to efficiently come into contact or contributes to improvement in the efficiency of transferring the flavor to the non-ignition end side.

According to the third embodiment, as for the size of the cup member 502, the diameter of the bottom plate 52 may be from 3 mm to 10 mm, preferably 4 mm to 8 mm, and the length in the direction from the ignition end to the non-ignition end (the height of the cup member 502) may be from 30 mm to 80 mm.

The same conditions as those according to the first embodiment can be applied as for the thicknesses of the side wall 51 and the bottom plate 52 of the cup member 502 and their ratios.

Similarly to the cup member 500 according to the first embodiment, the cup member 502 according to the third embodiment may be made of a material including pulp, a binder, and metal soap. The same conditions as those of the first embodiment may be applied as for the manufacturing method therefor, the elements of the cup member, and the composition of the materials. Similarly to the first embodiment, the cup member 502 may be an integrally molded product or obtained by adhering a plurality of parts previously obtained by molding.

As shown in FIG. 4, according to the third embodiment, the heat conduction member 4 and the cup member 502 are in abutment against each other.

The end of the side wall 51 of the cup member 502 on the non-ignition end side is opposed to and in contact with the end face of the filter 5 on the ignition end side. In this manner, when the flavor inhaler 102 is used, a flavor generated from a flavor source is passed through the space in the cup member 502 and the filter 5 and efficiently transferred into the oral cavity of the user.

According to the third embodiment, the holding member 1 and the filter 5 are connected by the connection member 7. The same connection member 7 as that of the first embodiment may be used.

The filter 5 may include a capsule 8 having an aromatic as a content.

The side wall of the cup member 502 may be tilted to have a tapered shape so that the diameter of the opening of the cup member 502 on the non-ignition end side is greater than the diameter of the bottom plate. Note that when the flavor inhaler is produced by rolling as described above, it is preferable that the side wall of the cup member 502 is not tilted to have a tapered shape.

According to the third embodiment, the same conditions as those according to the first embodiment may be applied as for the materials and the positional relations of the holding member 1, the combustion type heat source 2, the flavor source 3, the heat conduction member 4, and the filter 5.

A part of the features of the first and second embodiments and a part of the features of the third embodiment may be combined as appropriate to produce a flavor inhaler.

EXAMPLES

While the present invention will be described more specifically by way of examples, the present invention is not limited to the following description of the examples unless the same departs the spirit and scope of invention.

Experiment 1

Three integrally molded cup members were produced by the manufacturing process including the steps of adding 34.4% by weight of water based on 100% by weight of the total weight of pulp, a binder, and metal soap to a material including 64 weight parts of bleached pulp (NBKP Hinton manufactured by Prince George Pulp & Paper Mills), 34.4 weight parts of carboxymethyl cellulose (CMC) (F10LC manufactured by Nippon Paper Industries Co., Ltd.), and 1.6 weight parts of metal soap (calcium stearate), kneading the material after the addition of water to prepare a molding material, and filling the molding material into the cavity of a mold heated so that the temperature of the mold wall surface which forms the cavity is about 200° C.

One mg of pure water was dropped on the inner wall of each of the cup members using a pipet. The time measurement started simultaneously with the dropping, and the time until the dropped pure water permeated into the cup member was measured. Whether the cup member was permeated with water was visually determined. At the time, it was determined on the basis of whether visual inspection became impossible as droplets dropped on the inner wall of the cup member were absorbed by the cup member. Samples after the cup member was permeated with pure water were each measured for the generation of deformation caused by something. More specifically, it was visually determined whether the shape of the cup member deformed as compared with the shape of the cup member before the pure water was dropped.

As a result of the experiment, it took at least 30 seconds for the dropped pure water to permeate into each of the three cup members according to the reference example.

No deformation was observed in any of the three cup members according to the reference example between before and after the pure water permeation.

As can clearly be understood from the result, the samples had water-repellency and were prevented from deforming after absorbing the water.

Conclusion

When the flavor inhaler including the cup member according to the present invention is used, it is expected that the loss of aerosol caused as aerosol generated from a flavor source is condensed at the cup member and permeates into the cup wall surface is slight.

It is also expected that the cup member can be prevented from softening or deforming, which would otherwise be caused as aerosol generated from the flavor source adsorbs to the cup member.

Supplement

It is known that a lot of users use a flavor inhaler according to the following patterns.
Inhaling time per one puff: three seconds or less
Puff interval: 30 seconds or less It is estimated that the retention time of aerosol at the cup member is equal to the above.

The amount of aerosol per one puff generated under the above inhaling conditions is generally several mg or less.

Therefore, the experiment method and the result are based on a simulation of a phenomenon in which aerosol generated from the flavor source adsorbs to the cup member while the flavor inhaler is used.

Experiment 2

Test Samples

As an example, a flavor inhaler according to the first embodiment was produced with the cup member produced according to the above method.

As a comparative example, a flavor inhaler identical to the above-described sample disclosed in WO 2015/174442 except that a stainless steel cup disclosed in WO 2015/174442 was used as the cup member was produced.

The amounts of aerosol (TPM amounts) delivered from the example and the comparative example were measured by the following method.

Test Device

A test device disclosed in WO 2015/046420 was used as a measurement device. More specifically, the test device includes a suction pump, a mass flow controller (MFC), a valve controller, an electromagnetic valve, and a Cambridge filter. The end of each of the samples on the filter side is connected to the Cambridge filter, the tip end of a carbon heat source was ignited, then puff operation is carried out a prescribed number of times, and the amount of aerosol (TPM amount) collected to the Cambridge filter was measured.

More specifically, the electromagnetic valve was opened/closed by the valve controller, so that the suction pump and the Cambridge filter were connected for three seconds, and then the Cambridge filter was released into the air for 12 seconds. The operation as one puff operation was repeated ten times. Note that the flowrate of the mass flow controller was set to 1400 mL/min.

TPM Measurement Method

A value obtained by subtracting the weight of Cambridge filter before collecting aerosol from the weight of Cambridge filter after collecting the aerosol was set as an aerosol amount (TPM amount).

Result

As for the aerosol amounts (TPM amounts) measured by the above method, the average aerosol amount (TPM amount) per puff is given in the following.

Example: 1.92 mg/puff
Comparative Example: 2.05 mg/puff

Deformation of the cup member caused by softening was not observed after the sample of the example after ten puffing operations.

Conclusion

The aerosol delivery amount according to the example was substantially equal to that of the comparative example with the metal cup which would not allow permeation into the wall surface of the cup member. More specifically, it was confirmed that reduction in the aerosol delivery amount associated with the adsorption of aerosol generated from the flavor source while using the flavor inhaler having the cup member according to the invention was slight.

When the sample of the example after the puffing operation was visually inspected similarly to the reference example, reduction was observed in softening and deformation of the cup member which could be caused by the adsorption of aerosol generated from the flavor source to the cup member.

A cup member for storing a flavor source provided in a conventional flavor inhaler is made of a material including a metal such as stainless steel. In contrast, according to the present invention, a cup member made of a material including pulp, a binder, and metal soap is used as a member for storing a flavor source. In this way, the flavor inhaler may have a reduced weight or may be produced less costly. Furthermore, it can be expected that the presence of the metal soap in the material of the cup member prevents softening or deforming of the cup member which could be caused by the adsorption of aerosol from the flavor source to the cup member.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A cup member holding tobacco and/or an aerosol source for use in a flavor inhaler, comprising:
    a side wall; and
    a bottom plate,
    wherein at least the side wall and the bottom plate of the cup member is made of a material comprising pulp, a binder, and metal soap, and
    wherein the cup member is an integrally molded product of the material comprising the pulp, the binder, and the metal soap.

2. The cup member according to claim 1, wherein a number of carbons in a long chain fatty acid forming the metal soap is from 12 to 20, and wherein the metal is selected from calcium, magnesium, zinc, aluminium, and strontium.

3. The cup member according to claim 1 wherein the binder includes carboxymethyl cellulose or sodium carboxymethyl cellulose.

4. The cup member according to claim 1, wherein the metal soap is calcium stearate.

5. The cup member according to claim 1, wherein the weight ratio of the binder and the pulp in the cup member is from 25:75 to 70:30.

6. The cup member according to claim 1, wherein the bottom plate of the cup member has a thickness from 0.3 mm to 1.0 mm.

7. The cup member according to claim 1, wherein the bottom plate of the cup member is provided with ventilation holes.

8. The cup member according to claim 1, wherein the cup member has a flange protruding from an outer circumference of an opening of the cup member to outside of the cup member.

9. The cup member according to claim 1, wherein the cup member has a plurality of projections provided along an inner wall surface of the cup member.

10. The cup member according to claim 9, wherein the plurality of projections is provided at equal intervals along the inner wall surface of the cup member.

11. The cup member according to claim 7, wherein the cup member has a plurality of projections provided along an inner wall surface of the cup member, wherein at least some of the ventilation holes are provided in a position closer to the inner wall surface of the cup member than a minimum distance line connecting adjacent projections among the plurality of projections.

* * * * *